(12) United States Patent
Kiesele et al.

(10) Patent No.: US 6,607,642 B1
(45) Date of Patent: Aug. 19, 2003

(54) ELECTROCHEMICAL GAS SENSOR WITH DIAMOND-LIKE CARBON ELECTRODES

(75) Inventors: Herbert Kiesele, Lübeck (DE); Frank Mett, Lübeck (DE); Peter Tschuncky, Lübeck (DE)

(73) Assignee: Drägerwerk Aktiengesellschaft (DE)

( * ) Notice: Subject to any disclaimer, the term of this patent is extended or adjusted under 35 U.S.C. 154(b) by 80 days.

(21) Appl. No.: 09/635,328

(22) Filed: Aug. 9, 2000

(30) Foreign Application Priority Data

Aug. 17, 1999 (DE) .......................... 199 39 011

(51) Int. Cl.[7] ............................. G01N 27/404
(52) U.S. Cl. ...................... 204/415; 412/431
(58) Field of Search .................. 204/415, 431, 204/432, 412

(56) References Cited

U.S. PATENT DOCUMENTS

| | | | | |
|---|---|---|---|---|
| 3,239,444 A | * | 3/1966 | Heldenbrand | |
| 4,790,925 A | * | 12/1988 | Miller et al. | |
| 5,063,081 A | * | 11/1991 | Cozzette et al. | |
| 5,344,546 A | * | 9/1994 | Kiesele et al. | |
| 5,518,602 A | * | 5/1996 | Kessel | |
| 5,855,750 A | * | 1/1999 | Kiesele | |
| 5,906,718 A | * | 5/1999 | Hance et al. | |

FOREIGN PATENT DOCUMENTS

| | | |
|---|---|---|
| DE | 196 39 311 C2 | 4/1998 |
| DE | 197 45 486 A1 | 4/1999 |
| EP | 0 647 318 B1 | 4/1995 |

OTHER PUBLICATIONS

US published application 6,251,244 B1, Jun. 26, 2001.*
André Perret et al. 21/97 Carbon–Based Materials for Microdevices Materials for Microsystems.

* cited by examiner

Primary Examiner—T. Tung
(74) Attorney, Agent, or Firm—McGlew and Tuttle, P.C.

(57) ABSTRACT

An electrochemical gas sensor (1) is disclosed with a plurality of electrodes (2, 3, 4). The sensor has substantially reduced cross sensitivity with respect to interfering gases. At least the measuring electrode (2) is provided as a thin layer of diamond-like carbon (DLC, diamond-like carbon) on the gas-permeable membrane (9).

20 Claims, 1 Drawing Sheet

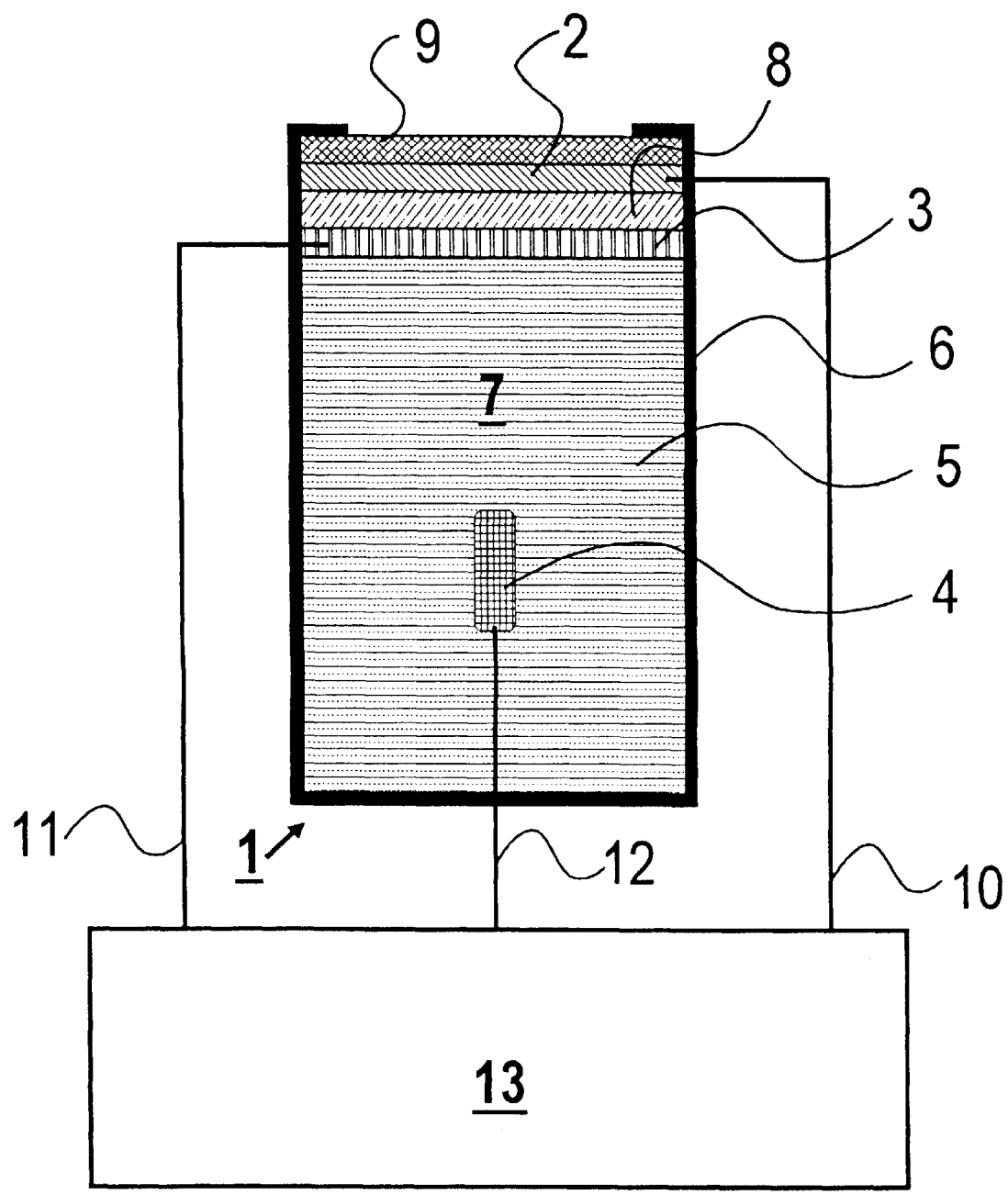

ELECTROCHEMICAL GAS SENSOR WITH DIAMOND-LIKE CARBON ELECTRODES

FIELD OF THE INVENTION

The present invention pertains to an electrochemical gas sensor with a plurality of electrodes, with an electrolyte and with a gas-permeable membrane.

BACKGROUND OF THE INVENTION

Such a gas sensor is described in DE 196 39 311 C2, in which the measuring electrode consists of a corrosion-resistant material from the platinum group or of gold.

Highly sensitive and reliable gas sensors are needed for the detection and the measurement of the concentration especially of toxic gases, electrochemical gas sensors being particularly suitable for many gases and because of their robustness and long service life.

Such electrochemical gas sensors must meet in practice a number of requirements, e.g.:

the basic current should be low;
the basic current should be affected by changes in the moisture content in the air and the air temperature as little as possible;
the measured signal should have the highest possible long-term stability;
the gas sensor should have the lowest possible cross sensitivity for interfering gases that occur together with the gas to be measured.

In particular, the requirement for the lowest possible cross sensitivity can be met only insufficiently in many cases for a gas sensor and for the corresponding measuring electrode while the other quality criteria are met.

SUMMARY AND OBJECTS OF THE INVENTION

The object of the present invention is therefore to propose an improved gas sensor that measures more selectively with reduced cross sensitivity with respect to interfering gases but has at the same time a short response time and high sensitivity for the gas to be measured, without its service life being reduced.

According to the invention, an electrochemical gas sensor is provided with a plurality of electrodes, with an electrolyte and with a gas-permeable membrane. At least the measuring electrode is a thin layer consisting essentially of diamond-like carbon (DLC, diamond-like carbon) on the gas-permeable membrane.

The thickness of the thin layer of diamond-like carbon may be 50 nm to 1,000 nm. The thin layer of diamond-like carbon may be produced by a coating process at room temperature, preferably by a sputtering process in a radio frequency magnetron sputtering unit. An adhesion promoter, especially a silicon-containing adhesion promoter, may be applied between the thin layer of diamond-like carbon and the gas-permeable membrane. The electrolyte may contain a mediator, which selectively engages in a rapid reaction with the gas to be measured, the reaction yielding a product that reacts in a rapid, especially diffusion-controlled reaction at the measuring electrode and whose concentration is an indicator of the concentration of the gas to be detected. The mediator may be LiBr or $Ag_2SO_4$. The gas-permeable membrane may be a perfluorinated polymer, especially PTFE (polytetrafluoroethylene), PFA (perfluoroalkoxy polymer) or FEP (copolymer of hexafluoropropylene and tetrafluoroethylene) or of one of the materials Cyclopore®, Isopore and Nuclepore®.

According to another aspect of the invention a process for using an electrochemical gas sensor is provided for detecting $F_2$, $Cl_2$, $ClO_2$, $Br_2$, $I_2$, $NO_2$, $H_2O_2$, $O_3$, $PH_3$, and $AsH_3$.

It was surprisingly observed in experiments that the properties of the gas sensor are sometimes greatly improved if the measuring electrode of an electrochemical gas sensor is designed in the form of a thin layer applied to the gas-permeable membrane preferably by means of a sputtering process in a magnetron from diamond-like carbon: Thus, the long-term stability is further improved, the influence of changes in the moisture content in the air and the air temperature on the basic current is reduced, and, in particular, the cross sensitivity to interfering gases is drastically reduced.

The essence of the present invention is that diamond-like carbon (DLC) is applied in a very thin layer to a gas-permeable membrane according to prior-art techniques. This arrangement is used in the gas sensor as a measuring electrode with a diffusion membrane arranged in front of it. The diamond-like carbon layer may be produced with an RF (radio frequency) magnetron sputtering process, but also by means of other coating methods. By selecting the process judiciously, it is possible to use both undoped and doped layers to improve the electric conductivity.

Even though diamond-like carbon layers (DLC, diamond-like carbon) have been used as an electrode material for some years now, as is apparent from the article "Carbon-Based Materials for Microdevices," *Microsensor Technology, mst news*, 21/97, pp. 14 through 16, André Perret et al., these layers were applied at high temperatures to gas-tight substrates, e.g., silicon, and were therefore unsuitable for use in gas sensors. It has been known from EP 0 647 318 B1 that a porous membrane can be coated with this material, but the use of the material layer according to the present invention as an electrode and especially as a measuring electrode is not embodied in this prior-art arrangement.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWING

In the drawings:

The only FIGURE is a schematic sectional view through an electrochemical gas sensor according to the invention;

DESCRIPTION OF THE PREFERRED EMBODIMENTS

Referring to the drawings in particular, the only FIGURE shows a schematic section through an electrochemical gas sensor 1 with general arrangement corresponding to DE 196 39 311 C2 as is especially suitable for the measurement of chlorine gas. The dimensions used are not true to scale and are shown, in general, enlarged for illustration. In the electrochemical gas sensor 1 according to the invention, the measuring electrode 2 consists of a thin layer of diamond-like carbon (DLC, diamond-like carbon), which is produced by a sputtering process on the gas-permeable membrane 9.

The thin layer of diamond-like carbon may be doped to improve the electric conductivity, especially with boron and/or nitrogen. The thickness of this layer is 50 nm to 1,000 nm and especially 100 nm to 500 nm. The counterelectrode 3 is formed of silver plate or silver fabric and the reference electrode 4 is formed of sintered silver powder.

The electrodes are arranged in the electrolyte chamber 5 of the gas sensor housing 6. The electrolyte chamber 5 is filled with an aqueous electrolyte 7 consisting essentially of lithium bromide, which also acts as a mediator at the same time. A separator 8 formed of glass fiber mat with a thickness of 0.3 mm is located between the measuring electrode 2 according to the present invention and the counterelectrode 3 in order to set a uniform distance between the electrodes 2, 3. The reference electrode 4 is fastened at a distance of a few mm from the electrodes 2, 3, so that its potential cannot be influenced by bromine. The gas sensor housing 6 is closed from the environment at the measuring electrode 2 with the gas-permeable membrane 9, through which the chlorine can diffuse to the measuring electrode 2. The measuring electrode 2, the counterelectrode 3 and the reference electrode 4 have measuring connections 10, 11, 12, which are led through the gas sensor housing 6 and are connected to an evaluating circuit 13 with a potentiostat, not shown in the figure.

The mode of operation of the gas sensor 1 is as follows: When chlorine gas is admitted to the gas-permeable membrane 9, chlorine diffuses through the measuring electrode 2 into the electrolyte 7 and oxidizes there the mediator lithium bromide. The bromine formed in the process is again reduced into $Br^-$ at the measuring electrode 2 and the bromine molecules not reacted at the measuring electrode 2 are captured at the counterelectrode 3 and react with the electrode material there to form silver bromide. The reference electrode 4 consisting of silver delivers a stable potential, because it is located protected behind the counterelectrode 3 and is not compromised by bromine molecules. The long-term stability and the reproducibility of the gas sensor 1 according to the present invention are further improved by the protected reference electrode 4.

The prior-art chlorine gas sensor was improved by the design of the measuring electrode 2 according to the present invention as a thin layer on the gas-permeable membrane 9 and was tested with respect to cross sensitivity to different gases. The cross sensitivity to $H_2S$, $H_2O_2$ and phosphine ($PH_3$) was reduced by one, at times even two to four orders of magnitude compared with the prior-art design with a measuring electrode 2 consisting of gold, platinum or indium, and the gas sensor 1 is thus improved. Perfluorinated polymers, such as PTFE, PFA, FEP, but also Cyclopore®, Isopore or Nuclepore®, are particularly suitable materials for the gas-permeable membrane; the latter materials consist of polycarbonate and polyester, respectively, and are provided with perforations in the nanometer range in a two-step process. It is a special feature of these membranes that they possess very accurate and reproducible properties and have, in general, layer thicknesses in the micrometer range.

In an especially preferred embodiment of the subject of the present invention, an adhesion promoter, especially one based on silicon, is located between the measuring electrode 2 designed as a thin layer consisting of diamond-like carbon and the gas-permeable membrane 9.

Auxiliary electrodes may likewise be prepared from diamond-like carbon and applied as a thin layer to a membrane.

While specific embodiments of the invention have been shown and described in detail to illustrate the application of the principles of the invention, it will be understood that the invention may be embodied otherwise without departing from such principles.

What is claimed is:

1. An electrochemical gas sensor, comprises:
   a gas sensor housing defining a electrolyte chamber;
   a plurality of electrodes arranged in the electrode chamber, said plurality of electrodes including a measuring electrode;
   an electrolyte in the electrolyte chamber; and
   a gas-permeable membrane closing said electrolyte chamber, said measuring electrode comprising a thin layer of diamond-like carbon on said gas-permeable membrane;
   a measuring connection connected to said measvring electrode; and
   an evaluating circuit including a potentiostat, said evaluating circuit being connected to said measuring connection.

2. An electrochemical gas sensor in accordance with claim 1, wherein the thickness of the thin layer of diamond-like carbon is 50 nm to 1,000 nm.

3. An electrochemical gas sensor in accordance with claim 2, wherein the thin layer of diamond-like carbon is produced by a coating process at room temperature.

4. An electrochemical gas sensor in accordance with claim 3, wherein an adhesion promoter is applied between the thin layer of diamond-like carbon and said gas-permeable membrane wherein said adhesion promoter contains silicon.

5. An electrochemical gas sensor in accordance with claim 4, wherein said electrolyte contains a mediator, which selectively engages in a rapid reaction with the gas to be measured, the reaction yielding a product that reacts in a rapid, especially diffusion-controlled reaction at said measuring electrode, a concentration of said product being an indicator of a concentration of the gas to be detected.

6. An electrochemical gas sensor in accordance with claim 2, wherein the thin layer of diamond-like carbon is produced with a sputtering process in a radio frequency magnetron sputtering unit.

7. An electrochemical gas sensor in accordance with claim 2, wherein said measuring electrode consists of the thin layer of diamond-like carbon wherein a silicon adhesion promoter is applied between the thin layer consisting of diamond-like carbon and said gas-permeable membrane.

8. An electrochemical gas sensor in accordance with claim 2, wherein said electrolyte contains a mediator, which selectively engages in a rapid reaction with the gas to be measured, the reaction yielding a product that reacts in a rapid, especially diffusion-controlled reaction at said measuring electrode, a concentration of said product being an indicator of a concentration of the gas to be detected.

9. An electrochemical gas sensor in accordance with claim 8, wherein the mediator is LiBr or $Ag_2SO_4$.

10. An electrochemical gas sensor in accordance with claim 1, wherein the thin layer of diamond-like carbon is produced by a coating process at room temperature.

11. An electrochemical gas sensor in accordance with claim 1, wherein the thin layer of diamond-like carbon is produced with a sputtering process in a radio frequency magnetron sputtering unit.

12. An electrochemical gas sensor in accordance with claim 11, wherein said electrolyte contains a mediator, which selectively engages in a rapid reaction with the gas to be measured, the reaction yielding a product that reacts in a rapid, especially diffusion-controlled reaction at said measuring electrode, a concentration of said product being an indicator of a concentration of the gas to be detected.

13. An electrochemical gas sensor in accordance with claim 1, wherein said measuring electrode consists of the thin layer of diamond-like carbon wherein an adhesion promoter is applied between the thin layer consisting of diamond-like carbon and said gas-permeable membrane.

14. An electrochemical gas sensor in accordance with claim 1, wherein said electrolyte contains a mediator, which selectively engages in a rapid reaction with the gas to be measured, the reaction yielding a product that reacts in a rapid, especially diffusion-controlled reaction at said measuring electrode, a concentration of said product being an indicator of a concentration of the gas to be detected.

15. An electrochemical gas sensor in accordance with claim 14, wherein the mediator is LiBr or $Ag_2SO_4$.

16. An electrochemical gas sensor in accordance with claim 1, wherein said gas-permeable membrane consists essentially of one of a perfluorinated polymer, Cyclopore®, Isopore, and Nuclepore®.

17. An electrochemical gas sensor in accordance with claim 16, wherein said perfluorinated polymer is one of polytetrafluoroethylene, perfluoroalkoxy polymer and copolymer of hexafluoropropylene and tetrafluoroethylene.

18. An electrochemical gas sensor, comprising:

a gas sensor housing defining an electrolyte chamber;

an electrolyte in the electrolyte chamber;

a gas-permeable membrane closing said electrolyte chamber to retain the electrolyte in the electrolyte chamber;

a measuring electrode consisting of a thin layer of diamond-like carbon of a thickness from 50 nm to 1,000 nm on said gas-permeable membrane in said electrolyte chamber;

a counterelectrode in said electrolyte chamber and positioned spaced from said measuring electrode;

a reference electrode spaced from said counterelectrode and spaced from said measuring electrode;

a measuring connection connected to said measuring electrode;

a counterelectrode measuring connection connected to said counterelectrode;

a reference electrode measuring connection connected to said reference electrode; and an evaluating circuit including a potentiostat, said evaluating circuit being connected to each of said measuring connection, said counterelectrode measuring connection and said reference electrode measuring connection.

19. An electrochemical gas sensor in accordance with claim 18, wherein a silicon adhesion promoter is applied between the thin layer consisting of diamond-like carbon and said gas-permeable membrane.

20. An electrochemical gas sensor in accordance with claim 18, wherein said electrolyte contains a mediator, which selectively engages in a rapid reaction with the gas to be measured, the reaction yielding a product that reacts in a rapid, especially diffusion-controlled reaction at said measuring electrode, a concentration of said product being an indicator of a concentration of the gas to be detected.

* * * * *